United States Patent [19]

Miller et al.

[11] Patent Number: 4,704,400

[45] Date of Patent: Nov. 3, 1987

[54] MEDICARPIN DERIVATIVES AND ANALOGS

[75] Inventors: Douglas K. Miller, Westfield, N.J.; Henry Joshua, Staten Island, N.Y.; Sharon J. Sadowski, Linden, N.J.

[73] Assignee: Merck & Co., Inc., Rahway, N.J.

[21] Appl. No.: 877,936

[22] Filed: Jun. 24, 1986

[51] Int. Cl.$^4$ ........................................ A61K 31/205
[52] U.S. Cl. .................................................. 514/454
[58] Field of Search ...................................... 514/454

[56] References Cited

PUBLICATIONS

Chem. Abst. 103-189180t (1985).
Chem. Abst. 104-95475m (1986).
Yukihiro Goda et al., *Chem. Pharm. Bull.*, vol. 33 (12), pp. 5606-5609, 1985.

*Primary Examiner*—Stanley J. Friedman
*Attorney, Agent, or Firm*—Theresa Y. Cheng; Michael C. Sudol

[57] ABSTRACT

Medicarpin derivatives and related pharmaceutical compositions and methods of treatment are disclosed. The compounds are useful as inhibitors of mammalian leukotriene biosynthesis. As such, they are useful therapeutic agents for treating allergic conditions, asthma, cardiovascular disorders and inflammation.

2 Claims, No Drawings

MEDICARPIN DERIVATIVES AND ANALOGS

BACKGROUND OF THE INVENTION

This invention involves certain medicarpin derivatives. These compounds are useful inhibitors of mammalian leukotriene biosynthesis. As such, they are useful therapeutic agents for treating allergic conditions, asthma, cardiovascular disorders and inflammation.

The leukotrienes are a novel group of biologically active mediators derived from arachidonic acid through the action of lipoxygenase enzyme systems. There are two groups of leukotrienes derived from the unstable Leukotriene $A_4$. The first of these are the peptido-lipid leukotrienes, the most important being Leukotrienes $C_4$ and $D_4$. These compounds collectively account for the biologically active material known as the slow reacting substance of anaphylaxis. The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., *Ann. Rpts. Med. Chem.* 17 203 (1982).

RESPIRATORY CONDITIONS (a) Asthma

The leukotrienes are potent spasmogens of human trachea, bronchus and lung parenchymal strips, and when administered to normal volunteers as aerosols are 3,800 times more potent than histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. 5-Lipoxygenase products are also thought to be regulators of mast cell degranulation and recent studies with human lung mast cells have suggested that 5-Lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amounts of leukotrienes. There is therefore good evidence that the leukotrienes are important mediators of human asthma. 5-Lipoxygenase inhibitors would therefore be a new class of drugs for the treatment of asthma. See for example, B. Samuelson, *Science* 220 568-575 (1983).

SKIN DISEASES (a) Psoriasis

Psoriasis is a human skin disease which effects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

ALLERGIC CONDITIONS (a) Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis and gall bladder spasms. In addition, they may have a role in cardiovascular disease because leukotrienes $C_4$ and $D_4$ act as coronary and cerebral arterial vasoconstrictors, and these compounds may also have negative inotropic effects on the myocardium. In addition, the leukotrienes are important mediators of inflammatory diseases through their ability to modulate leukocyte and lymphocyte function.

A number of medicarpin derivatives of the general Formula below are known:

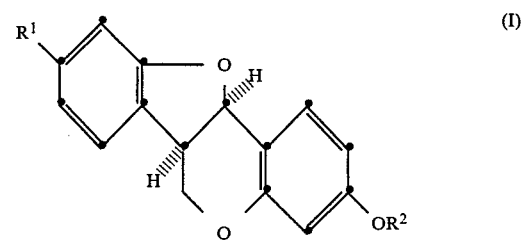

for example, medicarpin was described in *Plant Path.* 1: 41, 1971; *Phytopath.*, 58: 1377, 1968; 62: 1365, 1975 and 13: 291, 1974. It was isolated from *Dalbergia Odorifera T. Chen.* and showed negative results when tested for prostaglandin inhibition. However, none of these references discloses medicarpin or its analogs as inhibitors of mammalian leukotriene biosynthesis, nor does any one of these references teach that these compounds are useful for the treatment of asthma, allergies, inflammation and certain skin diseases.

SUMMARY OF THE INVENTION

This invention is directed to pharmaceutical compositions containing a compound of the Formula I:

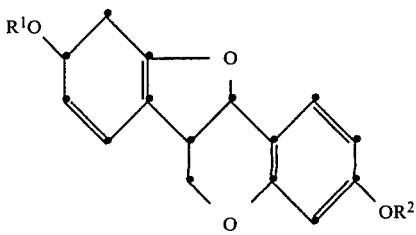

or a pharmaceutically acceptable salt thereof, a method of treatment using the composition and certain novel compounds of formula I.

DETAILED DESCRIPTION OF THE INVENTION

One embodiment of the present invention is a pharmaceutical composition containing a compound of the Formula I:

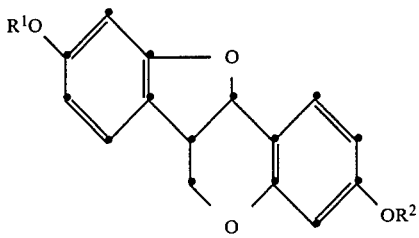

wherein
$R^1$ and $R^2$ independently are
(1) hydrogen; or
(2) alkyl having 1-6 carbon atoms.

The preferred compounds of Formula I are those wherein when $R^1$ is H, $R^2$ is $CH_3$ and vice versa.

The compounds of the Formula I have unexpected activity as inhibitors of the mammalian biosynthesis of leukotrienes. The compounds of Formula I therefore are expected to act as inhibitors of the mammalian 5-Lipoxygenase enzyme system of the arachidonic acid cascade. This inhibition of the mammalian biosynthesis of leukotrienes indicates that the compositions would be useful to treat, prevent or ameliorate, in mammals and especially in humans (1) pulmonary conditions including diseases such as asthma, (2) allergies and allergic reactions such as allergic rhinitis, contact dermatitis, allergic conjunctivitis and the like, (3) inflammation such as arthritides, (4) pain, (5) skin conditions such as psoriasis and the like and (5) cardiovascular conditions such as angina and the like.

Representative compounds of Formula I have been tested using the following assay to determine their mammalian leukotriene biosynthesis inhibiting activity and other relevant activities:

CXBG cells grown intraperitoneally in $CB_4B_6/F_1/J$ mice were washed 5 times in Dulbeccos phosphate buffered saline without calcium or magnesium, suspended in medium 199 (Gibco) at $2 \times 10^6$ cells/ml, and incubated 15 minutes at 37°. Inhibitor solutions in methanol were incubated with the cells (10 μl/600 μl cells), for 5 minutes at 37°, and the cells were stimulated with 60 μl A23187 (50 μg/ml) for 10 minutes at 37°. Aliquots were removed for measurement of leukotriene $C_4$ or thromboxane $B_2$ by enzyme immunoassay as previously reported (D. K. Miller, et al., J. Immunological Methods, 81, 169-185, 1985). The percentage inhibition was calculated by the following:

$$\% \text{ Inhibition} = 100 \times \frac{(pm \text{ sample } - \text{ uninhibited unstimulated control})}{(pm \text{ stimulated control } - \text{ uninhibited unstimmulated control})}$$

$IC_{50}$s were determined graphically.

TABLE I

Assay Results
Inhibition of CXBG leukotriene and prostoglandin production by (Iso)medicarpin

| Eicosanoid | $IC_{50}$ (mg/ml) |
|---|---|
| $LTC_4$ | 0.1 μg/ml |
| $TXB_2$ | >5 μg/ml |

The test results presented above show that representative compounds of Formula I inhibit the mammalian biosynthesis of leukotrienes and have representative pharmaceutical utility e.g., for asthma, pain and allergy.

The pharmaceutical compositions of the present invention will contain sufficient compound of Formula I in a dosage form suitable for inhibiting the mammalian biosynthesis of leukotrienes or, for the treatment desired. The effective concentration of the Formula I compound in the composition will vary as required by the mode of administration, dosage form and pharmacological effect and level desired. A general daily dosage of Formula I will range from about 10 μg to 100 mg/kg of body weight. This dosage may be administered in single or divided individual doses. More or less of the general daily dosage may be necessary depending upon the individual needs of the patient.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release capsules and the like. Parenteral dosage forms include solutions, emulsions and the like. Dosage forms for administration by inhalation including sprays, aerosols and the like. These inhalation formulations may be administered in metered doses ranging from about 0.1 μg to about 200 μg, administered as needed.

For treating allergies or allergic reactions, such as allergic conjunctivitis, allergic rhinitis and the like, the Formula I compound may be administered by any conventional mode, e.g., orally, parenterally, topically, subcutaneously, by inhalation and the like. The oral and parenteral dosage forms are the same type as for the pulmonary treatment. The topical application dosage forms include ointments, salves, controlled release patches, emulsions, solutions, thixotropic formulations, powders, sprays and the like. For topical application, the percent by weight active ingredient (Formula I compound) may vary from about 0.001 to about 10%.

For treating inflammation the mode of administration may be oral, parenteral, by suppository and the like. The various dosage forms are the same as those described above.

For treating skin diseases such as psoriasis, atopic dermatitis and the like, oral, topical or parenteral administration is useful. For topical application to the diseased area salves, patches, controlled release patches, emulsions, etc., are convenient dosage forms.

For use as an analgesic, i.e., for treating pain, any suitable mode of administration may be used, e.g., oral, parenteral, by insufflation, by suppository and the like.

For treating cardiovascular conditions such as angina pectoris, etc., any suitable mode of administration, e.g. oral, parenteral, topical, insufflation, etc. and dosage form e.g. pills, liquid formulations, controlled release capsules, controlled release skin patches, etc. may be used.

In addition to the common dosage forms set out above, the compound of Formula I may also be administered for the various utilities and indications or for inhibiting leukotriene synthesis by controlled release means and/or delivery devices such as those described in U.S. Pat. Nos. 3,845,770; 3,916,899; 3,536,809; 3,598,123; 3,630,200 and 4,008,719.

Dosage forms for application to treat the eye are also disclosed in U.S. Pat. No. 4,348,398.

In preparing suitable dosage forms, conventional compounding procedures and ingredients e.g. diluents, carriers, etc. may be used. The following are examples of representative pharmaceutical dosage forms:

| Injectible Suspension | mg/mL |
| --- | --- |
| Compound of Formula I | 1-100 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |

| Aerosol for Oral Inhibition | mg/can (200 doses/can) |
| --- | --- |
| Compound of Formula I | 2-40 |
| Oleic Acid | 0.2-4.0 |
| Trichloromonofluoro methane | 5,000-8,000 To a total |
| Dichloromonofluoro methane | 15,000-12,400 of 20,400 |

| Cream | mg/g |
| --- | --- |
| Compound of Formula I | 1-100 |
| Cetyl alcohol | 130.0 |
| Sodium Lauryl Sulfate | 15.0 |
| Propylene Glycol | 100.0 |
| Methyl paraben | 1.8 |
| Propyl paraben | 1.2 |
| Purified Water of sufficient quantity to make total 1 g | |

| Ointment | mg/g |
| --- | --- |
| Compound of Formula I | 1-100 |
| Methyl paraben | 1.8 |
| Propyl paraben | 1.2 |
| Petrolatum of sufficient quantity to make total 1 g | |

| Tablet | mg/table |
| --- | --- |
| Compound of Formula I | 0.2-350 |
| Microcrystalline Cellulose | 0-349.8 |
| Providone | 14.0 |
| Microcrystalline Cellulose | 90.0 |
| Pregelatinized Starch | 43.5 |
| Magnesium Stearate | 2.5 |
| | 500 |

| Capsule | mg/capsule |
| --- | --- |
| Compound of Formula I | 0.2-350 |
| Lactose Powder | 248.5-598.3 |
| Magnesium Stearate | 1.5 |
| | 600 |

Examples showing the isolation and purification of the compounds of this invention are described below. These examples are provided merely as an aid to understand the instant invention. No limitation is intended, other than those that appear in the appended claims. All temperatures are in degrees Celsius and are uncorrected.

ISOLATION OF (ISO)MEDICARPIN

The dried chloroform extract of Dalbergiae Odoriferae comprising approximately 1.5 gm of viscous material was triturated with 8 ml methanol and centrifuged.

The supernatent was charged to a 1 inch I.D. by 2.2 meter long column filled with Sephadex LH-20 in methanol. The column was eluted at about 25° C. (temperature may range from room temperature to 50°) with methanol and CXBG active fractions eluting between 1.35 and 1.50 column volumes were concentrated yielding 116 mg of residue. Twenty-five mg of this residue was further fractionated by preparative reverse phase HPLC using a gradient from 30% to 100% acetonitrile at 40° C. (temperature may range from room temperature to 50° C.). The CXBG active fractions were combined yielding 14 mg of essentially pure (iso)medicarpin as determined by isocratic analytical HPLC., U.V., nmr and mass spectroscopy spectra.

What is claimed is:

1. A method of treating or preventing leukotriene-induced diseases which comprises administering to a patient in need of such treatment an effective amount of a Compound of formula I;

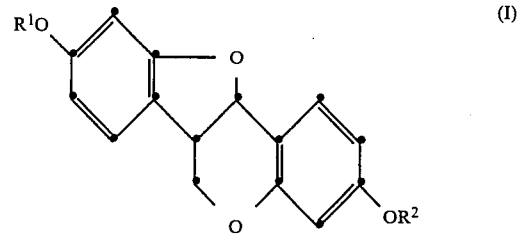

wherein:
$R_1$ and $R_2$ independently are:
(1) hydrogen; or
(2) alkyl having 1-6 carbon atoms.

2. The method of claim 1 wherein the active compound is medicarpin or isomedicarpin.

* * * * *